(12) United States Patent
Weinstein et al.

(10) Patent No.: US 6,294,178 B1
(45) Date of Patent: Sep. 25, 2001

(54) METHOD AND DEVICE FOR COORDINATING TOPICAL AND ORAL SINUSITIS TREATMENTS

(76) Inventors: Robert E. Weinstein, 177 Commonwealth Ave., Boston, MA (US) 02116; Allan M. Weinstein, 9205 Pegasus Ct., Potomac, MD (US) 20854

(*) Notice: Subject to any disclaimer, the term of this patent is extended or adjusted under 35 U.S.C. 154(b) by 0 days.

(21) Appl. No.: 09/431,806

(22) Filed: Nov. 1, 1999

(51) Int. Cl.[7] .............................. A61K 9/00; A61K 9/48; A61K 9/20; A61K 9/14; A61L 9/04
(52) U.S. Cl. .................. 424/400; 424/451; 424/464; 424/489; 424/45; 424/46; 424/405
(58) Field of Search ............... 424/45, 405, 408, 424/434, 435, 464, 489, 400, 439, 451, 10.1, 10.2; 206/534; 514/826, 853, 885, 929, 958

(56) References Cited

U.S. PATENT DOCUMENTS

| | | | |
|---|---|---|---|
| 5,492,689 | * | 2/1996 | Gwaltney, Jr. .................... 424/45 |
| 5,830,490 | * | 11/1998 | Weinstein et al. .................. 424/405 |

FOREIGN PATENT DOCUMENTS 830269   5/1938   (FR).

* cited by examiner

*Primary Examiner*—Thurman K. Page
*Assistant Examiner*—Blessing Fubara
(74) *Attorney, Agent, or Firm*—Robert R. Deleault, Esq..; Mesner & Deleault, PLLC

(57) ABSTRACT

A sinusitis treatment system having an oral dosage constituent, a topical nasal dosage constituent, indicia and instructions for administration of the oral dosage constituent and the topical nasal dosage constituent as an at least ten-day sinusitis treatment regimen.

21 Claims, 3 Drawing Sheets

Fig. 2

METHOD AND DEVICE FOR COORDINATING TOPICAL AND ORAL SINUSITIS TREATMENTS

BACKGROUND OF THE INVENTION

1. Field of the Invention

The present invention relates to a method and device for organizing and coordinating combined aerosol and oral medications for treating sinusitis.

2. Description of the Prior Art

Packaging has been developed for aiding the users of drugs to comply with administration. Dispensing apparatus associated with multiple day administrative drugs are typically directed to the administration of oral pills or capsules, or similar solid medication.

U.S. Pat. No. 4,039,080, for example, discloses a tray having individual compartments for pills which may contain a week's medication with indicia indicating the day of the week and the time of the day the medication is to be taken.

U.S. Pat. No. 4,553,670 discloses another device comprising a support on which are located two different ingestible medical substances in a single dose form with an adjacent portion for instructional information.

U.S. Pat. No. 4,593,819 discloses a covered pill tray of rectangular configuration having an array of open-topped compartments to hold a supply of medication arranged by the day and time of taking the medication.

U.S. Pat. No. 5,830,490 discloses a method and device for organizing, storing, instructing, and coordinating the combined use of aerosol and oral medications for the treatment of disorders including respiratory tract disorders such as rhinitis and asthma in order to reduce medication error and increase therapeutic compliance.

While the market place abounds with pill boxes and organizers for oral medications and while an organizational tool is presently available for a lay person to organize topical medications with oral medications, none of the prior art specifically claims a system for treating sinusitis.

Therefore, what is needed is a device that combines topical and oral modalities of treatment for sinusitis. What is further needed is a method for enhancing compliance of combined therapeutic regimens for treatment of sinusitis.

SUMMARY OF THE INVENTION

It is an object of the present invention to provide a system that combines topical and oral modalities of treatment for sinusitis. It is another object of the present invention to provide a method for enhancing compliance of combined therapeutic regimens for treatment of sinusitis. It is a further object of the present invention to provide patients and caregivers with expertly formulated and expertly instructed prepackaged sinusitis treatment regimens and to minimize both caregiver and user uncertainty with regard to appropriate sinusitis treatment. It is still a further object of the present invention to minimize the caregiver's task of instructing sinusitis treatments, particularly the time that is now required to instruct coordinated treatments with single agents which are individually prescribed and individually instructed. It is yet a further object of the present invention to simplify, organize and encourage compliance with the full course of combined oral/topical sinusitis regimens.

The present invention achieves these and other objectives by providing a system which combines topical and oral modes of treatment for sinusitis and for enhancing compliance with combined therapeutic regimens for sinusitis. The device consists of a unifying container which is prepackaged for a user and which incorporates at least one oral antibiotic, at least one topical agent, and indicia and instructions which instruct their coordinated use as a therapeutic regimen.

Sinusitis refers to infection of the paranasal sinuses which develops in approximately 31 million Americans each year. Acute sinusitis typically follows a viral upper respiratory infection or allergic reaction. Swelling of the nasal mucous membranes and obstruction of drainage from the sinus outflow tracts is thought to cause mucous to collect in the paranasal sinuses and become infected. Treatment is typically comprised of killing the overgrown bacteria with antibiotics, and reversing obstruction of drainage from the sinuses to restore the orderly flow of mucous secretions.

Antibiotic treatments for sinusitis are generally administered in an oral form for systemic distribution to accomplish penetration into the tissues. Antibiotics which are presently useful for treating organisms which infect the sinuses include: penicillins (ex: amoxicillin, amoxicillin-clavulanate), sulfas (ex: sulfamethoxazoletrimethoprim, erythromycin-sulfisoxazole), erythromycin analogues (ex: azithromycin, clarithromycin), cephalosporins (ex: cefaclor, cefuroxime axetil, cefpodoxime proxetil, cefprozil, cefixime, ceftibuten), carbacefems (ex: loracarbef), quinolones (ex: ciprofloxacin, levofloxacin), clindamycin, and metronidazole. The inclusion of other oral agents useful in the treatment of sinusitis, including decongestants (example are pseudoephedrine and phenylpropanolamine), antihistamines (examples are chlorpheniramine and diphenhydramine), moisturizing agents (for example, guiafenesin), and anticholinergic agents (for example, methscopolamine), is within the scope of the invention.

Topical treatments are useful in sinusitis because of the accessibility of the nasal membranes to direct applications. An advantage of topical treatments is that systemic side effects can be minimized. Useful topical agents for treating sinusitis include alpha-adrenergic decongestants which act to shrink mucous membranes and increase the patency of the sinus ostia (examples are phenylepherine and oxymetazoline), topical glucocorticoids which inhibit local inflammation (examples are beclomethasone, budesonide, and flunisolide nasal aerosols), and liquefying and moisturizing nasal instillations which facilitate mucous flow (examples are saline, hypertonic saline, propylene glycol, and polyethylene glycol). Topical treatments may be applied by aerosol sprays, drops, or lavages. Antihistamines and anticholinergic agents may be selectively useful either orally or topically in particular situations, for example, when sinusitis occurs as a complication of allergy, and are within the scope of the present invention.

Health care experts estimate that half of the 1.8 billion prescription medications dispensed yearly are not taken as prescribed. Adherence to medication is considered to be adversely affected by inconvenience and complexity of use. Conversely, compliance and the risk of medication error are improved with measures to increase convenience, establish simplicity, and reduce confusion. Poor compliance and error are particularly acknowledged to occur with topical aerosol treatments utilized for respiratory disorders.

Compliance with treatment is important in sinusitis. Individuals with sinusitis are typically required to follow through with treatments over at least a ten-day period. Premature discontinuation of treatment is known to result in an increased likelihood of relapse and complication. Failure of treatment can lead to chronic sinus infection and infection in areas adjacent to the sinuses, including the meninges and brain. Measures which facilitate treatment and encourage completion and success are therefore clearly worthwhile.

Multiple therapeutic components may be a source of confusion and frustration to users. Individual components lack indicia signifying use of the components together and components may be lost, misplaced, or ignored. Instructions issued separate from medication, as by the physician, may be lost. Furthermore, in spite of careful oral and written instructions from a health care provider, many patients are known to use what they have conveniently available. Haphazard applications of medication can result in treatment failure and in the requirement for additional medical attention and cost.

Cost factors and outcomes are carefully considered in the current medical climate. Improvements in organization and teaching including devices and methods, which would facilitate treatments, are considered desirable in view of limitations in time and costs for medical personnel. Successful therapy is less costly than unsuccessful treatment, which can lead to complications, multiple clinic visits, or hospitalizations.

The present invention provides a device and method for treating sinusitis employing a unifying dispensing container which incorporates at least one topical agent, at least one oral antibiotic, and expertly devised indicia and instructions for directing the user to coordinate the use of the agents as a therapeutic regimen. The medications, indicia and instructions are therefore devised by experts in the art and prepackaged for both the caregiver and lay user. It is to be understood that multiple doses of at least one oral agent which includes an antibiotic, and multiple doses of at least one topical agent are contained within the device. The oral dosage may be in the form of tablet, pill, capsule, caplet, packets or containers of liquids, gels, or solids, some of which may require reconstituting, or any generally recognized oral medication form. Preferably, the topical agent is in fully constituted form and applied by aerosol, drop or lavage to the nasal membranes. Alternatively, topical agents may be supplied in a form requiring reconstitution. The topical agent is preferably contained within an applicator device such as a spray or dropper bottle, but may alternatively be supplied separately and require transfer to the applicator device.

BRIEF DESCRIPTION OF THE DRAWINGS

FIG. 2 is a plan view of another container in accordance with the present invention.

DETAILED DESCRIPTION OF THE PREFERRED EMBODIMENT

The following detailed description of the invention is provided to aid those skilled in the art in practicing the present invention, however, it should not be construed to unduly limit the present invention. Variations and modifications in the disclosed embodiments may be made by those of ordinary skill in the art without departing from the scope of the present invention. With regard to the drawings, it will be understood that while preferred embodiments of the invention have been illustrated and described, the invention is not limited to such embodiments. Changes and additions may be made without departing from the spirit of the invention.

Figure 1:
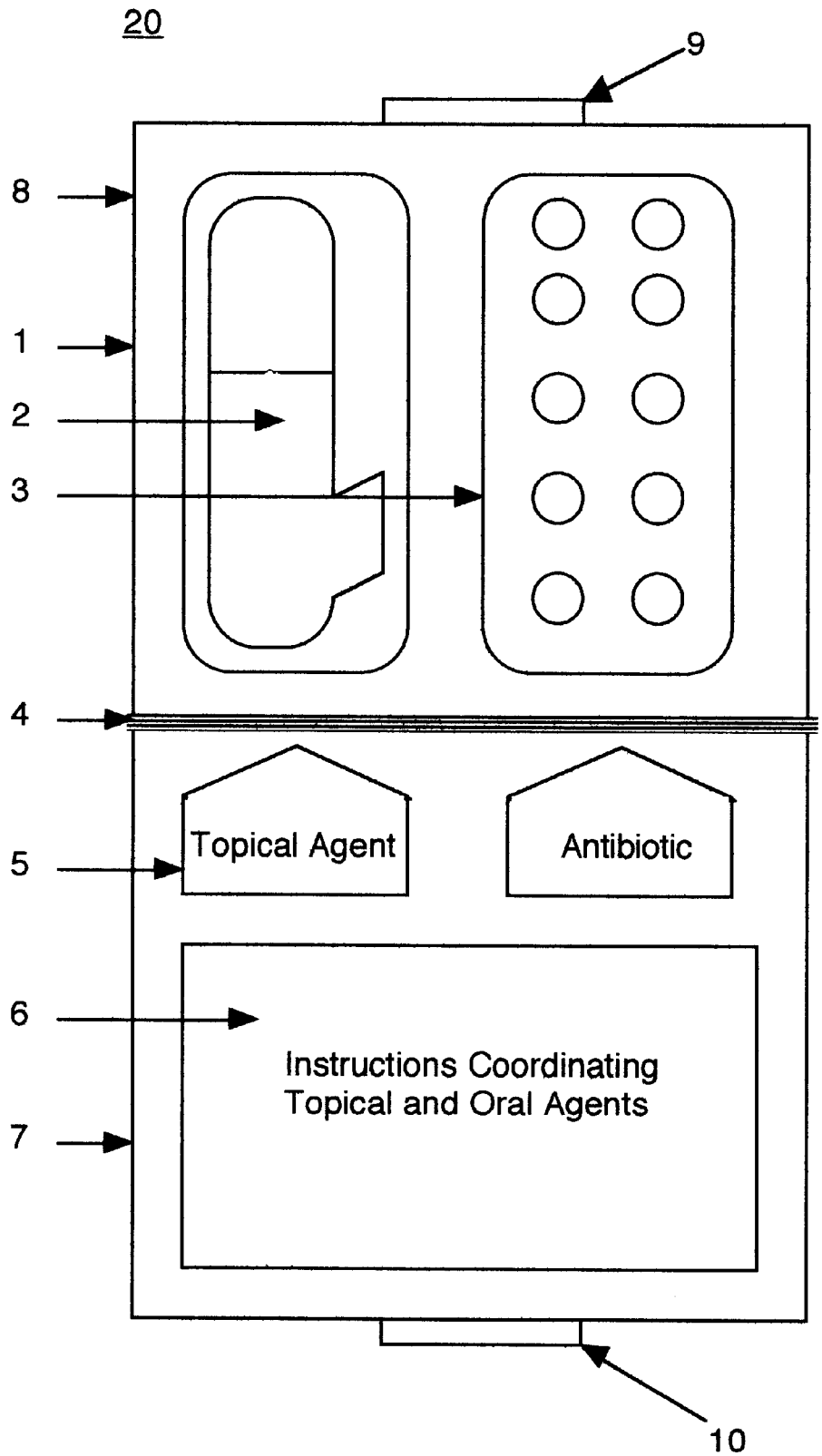
FIG. 1 is a plan view of a container in accordance with the present invention.
Figure 2:
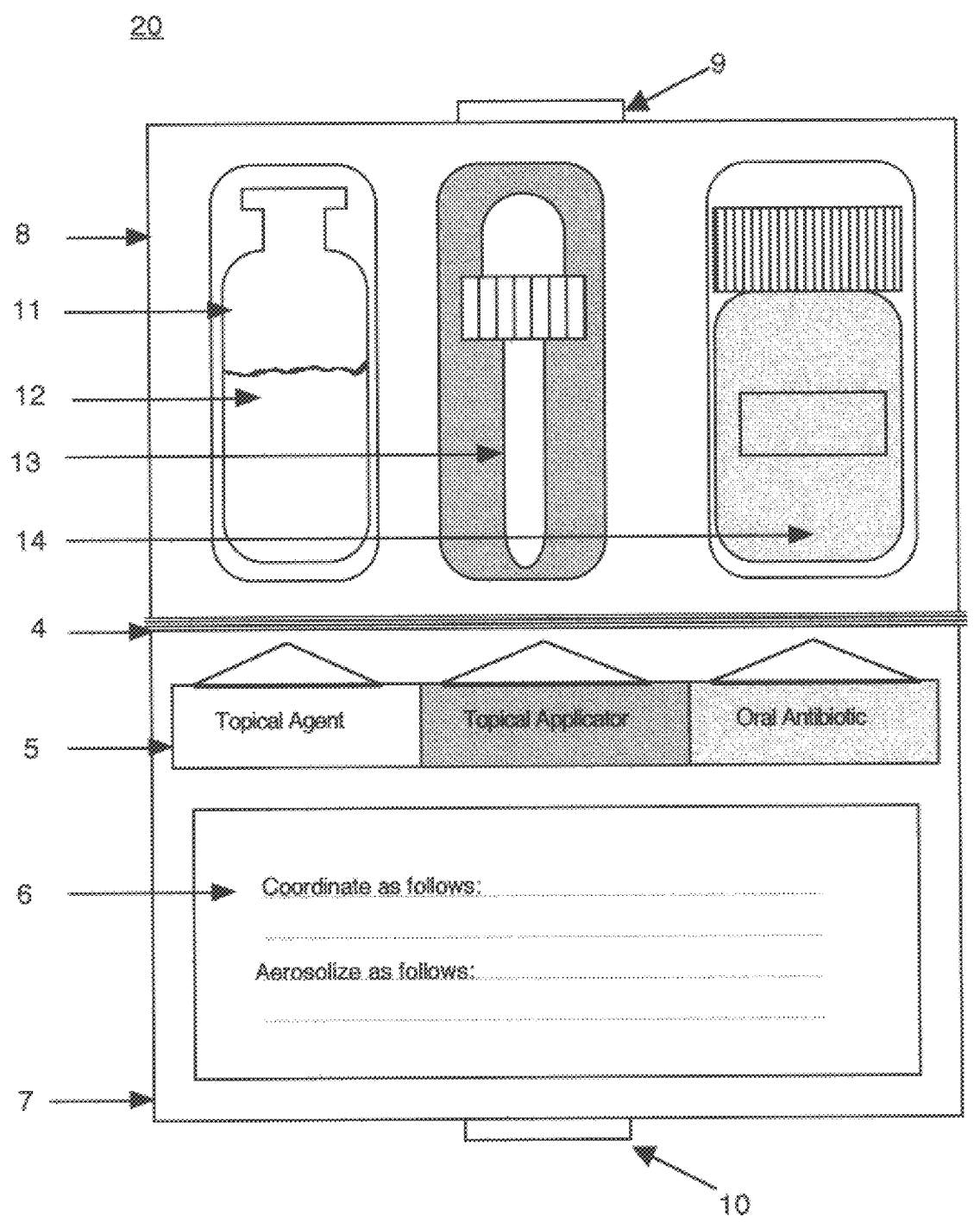
Figure 3:
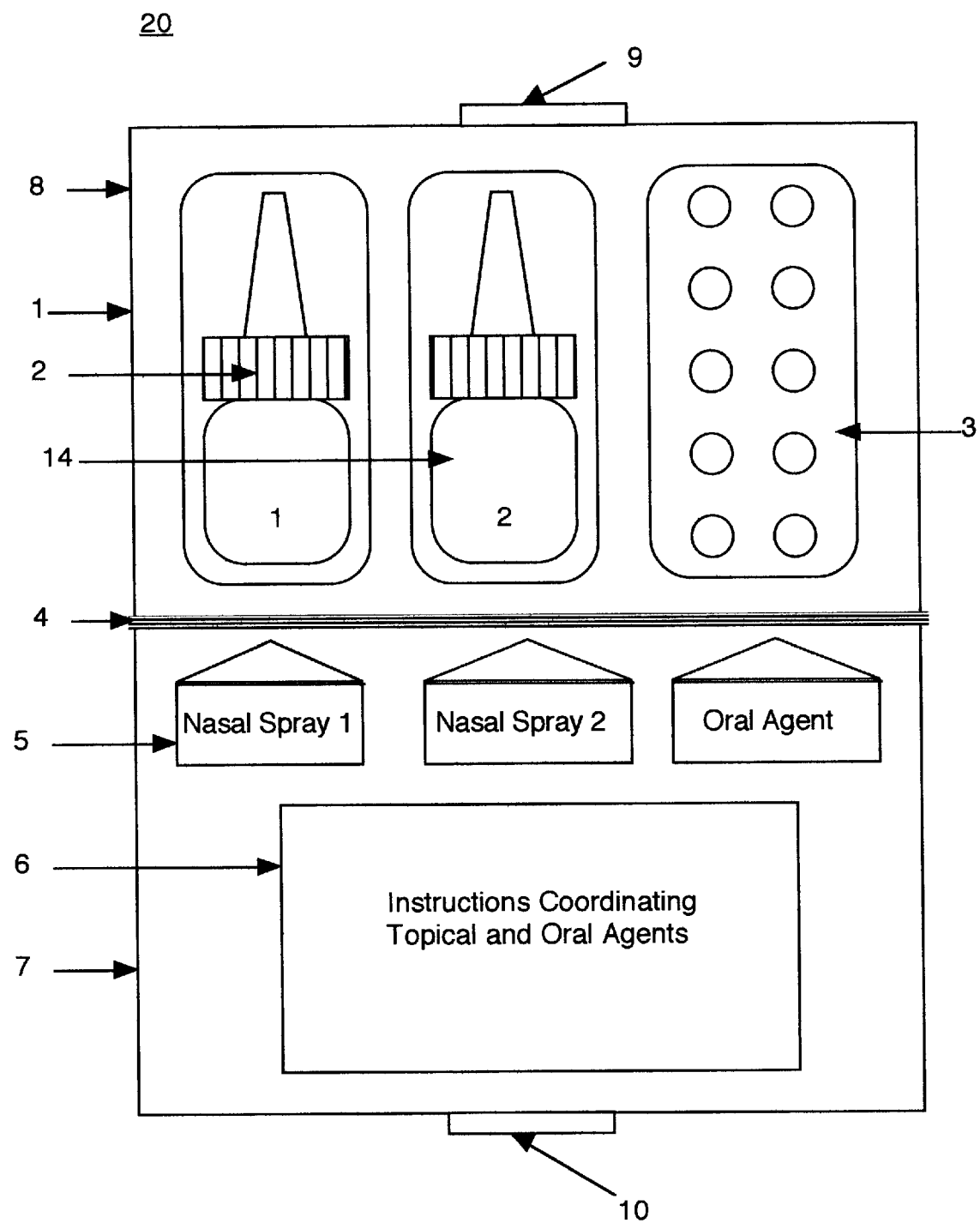
FIG. 3 is a plan view of another container in accordance with the present invention.

Three embodiments of the unifying container of the preferred invention are depicted in FIGS. 1–3. FIG. 1 depicts a sinusitis treatment system 20 in a support package 1. Support package 1 has a first portion 7 and a second portion 8. Second portion 8 houses dosages of a topical agent in an applicator device 2 and dosages of an oral antibiotic in the form of tablets in a blister wrap 3. Techniques for making and attaching such wraps is well known and will not therefore be further described. A fold 4 in the package is provided in the center between first portion 7 and second portion 8. Identifying indicia 5 is provided with respect to the topical agent and antibiotic. Identifying indicia 5 may be provided on either first portion 7 or second portion 8, or on the immediate package of the agents, or on the agents themselves such as by color, shape, size, etc. First portion 7 houses an instruction-bearing portion 6 that provides instructions coordinating use of the topical and oral medication. The first portion 7 and the second portion 8 of the support package each contain respective clasp portions 9 and 10 which can be secured together when support package 1 is folded along fold 4. Other containers, such as a conventional folding paper box, and other closures are within the scope of the invention.

FIG. 2 depicts another embodiment of sinusitis treatment system 20. System 20 contains a support package 1 having a first portion 7 and a second portion 8. Second portion 8 contains a reservoir 11 enclosing dosages of a topical agent, a device 13 for applying the topical agent, and multiple dosages of oral antibiotic in a capped container 14. The reservoir 11 enclosing multiple doses of the topical agent may consist of a vial, bottle, canister, or other container suitable for containing and transferring liquid. Applicator devices for applying the topical agent may include conventional dropper bottles, nasal lavage apparatus, aerosol squeeze sprayers, and aerosol nebulizers, such as hand-held metered dose nebulizers as are known in the art. Identifying indicia 5 is provided with respect to the topical agent, the topical applicator and the oral antibiotic. Identifying indicia 5 may be provided on either first portion 7 or second portion 8. First portion 7 houses an instruction-bearing portion 6 that provides instructions coordinating use of the topical and oral medication. The instruction-bearing portion 6, in this instance, includes instructions for transferring the topical agent from the reservoir 12 to the applicator device 13, as well as for applying the topical agent with applicator device 13. First portion 7 and second portion 8 of support package 1 each contain respective clasp portions 9 and 10 which can be secured together when support package 1 is folded along fold 4.

FIG. 3 depicts yet another embodiment of sinusitis treatment system 20 with dosages of one oral antibiotic 3, and two topical agents 2 and 14, in accordance with the regimen exemplified as Sinusitis Treatment Regimen 2. System 20 includes a support package 1 having a first portion 7 and a second portion 8. Second portion 8 contains two separate combination reservoir/applicator combinations 2 and 14 enclosing dosages of two different topical agents. Second portion 8 also contains multiple dosages of oral antibiotic in the form of tablets in a blister wrap 3. Identifying indicia 5 is provided with respect to the topical agents and the oral antibiotic. Identifying indicia 5 may be provided on either first portion 7 or second portion 8. First portion 7 houses an instruction-bearing portion 6 that provides instructions coordinating use of the topical and oral medications. The instruction-bearing portion 6, in this instance, includes instructions for applying the topical agents in sequence. First portion 7 and second portion 8 of support package 1 each contain respective clasp portions 9 and 10 which can be secured together when support package 1 is folded along fold 4.

Packaging containing additional numbers of topical and/or oral agents is also within the scope of the present invention. The packaging may be adapted by widening the packaging and increasing the number of housings and indicia. Additionally, the packaging may be in any geometric configuration, particularly to incorporate applicator devices, as may be desired.

The invention will be further clarified by a consideration of the following examples, which are not inclusive, but rather intended to be exemplary:

EXAMPLE 1

Sinusitis Treatment Regimen 1

Sulfamethoxazole/trimethoprim 800/160 mg, one tablet every 12 hours for 10 days.

Beclomethasone Nasal Aerosol, two sprays in each nostril every 12 hours for 10 days.

This regimen employs dosing with the oral antibiotic sulfamethoxazole/trimethoprim to reverse bacterial overgrowth, particularly for individuals who are allergic to penicillin antibiotics. Dosing with the topical corticosteroid, beclomethasone, is employed to reverse local inflammation, swelling, and obstruction to mucous flow.

EXAMPLE 2

Sinusitis Treatment Regimen 2

Amoxicillin 250 mg, one capsule three times a day for 10 days

Phenylephrine HCl 0.5% nasal spray, 2 sprays in each nostril three times a day, for the first three days of treatment.

Buffered saline nasal spray, 2 sprays in each nostril three times a day, for subsequent seven days of treatment following treatment with phenylephrine.

This regimen employs ten days of dosing with the oral antibiotic amoxicillin to reverse bacterial overgrowth, and dosing with the topical decongestant, phenylepherine, to reverse local swelling and obstruction to mucous flow. Phenylepherine is discontinued after three days because of the known side effect of rebound nasal congestion which may follow longer use, and dosing with topical saline is thereafter employed to liquefy the mucous and promote drainage through the end of the ten day treatment course.

EXAMPLE 3

Sinusitis Treatment Regimen 3

Amoxicillin/Clavulanate 250/125 mg, one capsule three times a day for 10 days.

Pseudoephedrine HCl 120 mg, one capsule twice a day for 10 days.

Buffered saline nasal spray, 2 sprays in each nostril three times a day, for 10 days.

This regimen employs ten days of dosing with the oral antibiotic combination amoxicillin/clavulanate to reverse bacterial overgrowth, dosing with the oral decongestant pseudoephedrine hydrochloride to decrease congestion of the nasal and sinus membranes, and dosing with topical saline to liquefy the mucous and promote drainage throughout the course of treatment.

Other variations may occur to those skilled in the art which are within the scope of the invention as set forth in the appended claims. Those of skill in the art may also recognize modifications to these presently disclosed embodiments. These variations and modifications are meant to be covered by the spirit and scope of the present claims.

What is claimed is:

1. A sinusitis treatment system comprising:
    an oral dosage which includes an antibiotic, said oral dosage having a sufficient quantity to provide at least a ten-day treatment;
    a topical nasal dosage;
    indicia and instructions for the administration of said oral dosage and said topical nasal dosage as an at least ten-day regimen; and
    a container housing said oral dosage, said topical nasal dosage, said indicia, and said instructions.

2. The treatment system of claim 1 wherein said topical nasal dosage includes a sufficient quantity to provide treatment for at least ten days.

3. The treatment system of claim 1 which includes at least two different nasal dosages.

4. The treatment system of claim 3 wherein said at least two different nasal dosages includes a sufficient quantity to provide treatment for ten days according to said instructions for administration.

5. The treatment system of claim 1 wherein said oral dosage is in the form of a tablet, pill, capsule, caplet, liquid, powder or gel.

6. The treatment system of claim 1 wherein said topical nasal dosage is in the form of an aerosol.

7. The treatment system of claim 1 wherein said topical nasal dosage is in the form of a nose drop.

8. A sinusitis treatment system comprising:
    an oral dosage which includes an antibiotic wherein said oral dosage contains a sufficient quantity to provide treatment for at least ten days;
    a topical nasal dosage which includes at least one therapeutic agent selected from the class consisting of a decongestant, a moisturizing agent, a corticosteroid, an anticholinergic agent, and an antihistamine;
    indicia and instructions for the administration of said oral dosage and said topical nasal dosage as an at least ten-day sinusitis treatment regimen; and
    a container prepackaged for a user and housing said oral dosage, said topical nasal dosage, said indicia, and said instructions.

9. The treatment system of claim 8 wherein said moisturizing agent is one of saline, hypertonic saline, propylene glycol, and ethylene glycol.

10. The treatment system of claim 8 wherein said oral dosage is in the form of a tablet, pill, capsule, caplet, liquid, powder or gel.

11. The treatment system of claim 8 wherein said topical nasal dosage is in the form of an aerosol.

12. The treatment system of claim 8 wherein said topical nasal dosage is in the form of a nose drop.

13. A method of making a sinusitis treatment system, said method comprising:
    formulating an oral dosage which includes an antibiotic wherein said oral dosage contains a sufficient quantity to provide treatment for at least ten days;
    formulating a topical nasal dosage wherein said topical nasal dosage has one or more therapeutic agents;
    devising indicia and instructions for the administration of said oral dosage and said topical nasal dosage as an at least ten-day sinusitis treatment regimen; and providing a container for housing said oral dosage, said topical nasal dosage, said indicia, and said instructions therein.

14. A method of treating sinusitis, said method comprising:
  providing a combined topical and oral therapeutic regimen contained within a unified housing comprising:
    an oral dosage which includes an antibiotic, said oral dosage having a sufficient quantity to provide treatment for at least ten days;
    a topical nasal dosage; and
    indicia and instructions for the administration of said oral dosage and said topical nasal dosage as an at least ten-day regimen; and
  administering said oral dosage and said topical nasal dosage according to said instructions.

15. A method of treating sinusitis, said method comprising:
  providing a combined topical and oral therapeutic regimen contained within a unified housing comprising:
    an oral dosage which includes an antibiotic, said oral dosage having a sufficient quantity to provide treatment for at least ten days;
    a topical nasal dosage which includes at least one therapeutic agent selected from the class consisting of a decongestant, a moisturizing agent, a corticosteroid, an anticholinergic agent, and an antihistamine; and
    indicia and instructions for the administration of said oral dosage and said topical nasal dosage as an at least ten-day regimen; and
  administering said oral dosage and said topical nasal dosage according to said instructions.

16. The method of claim 15 wherein said moisturizing agent is at least one of saline, hypertonic saline, polypropylene glycol, and polyethylene glycol.

17. The method of claim 15 wherein said oral dosage is in the form of a tablet, pill, capsule, caplet, liquid, powder or gel.

18. The method of claim 15 wherein said topical nasal dosage is in the form of an aerosol.

19. The method of claim 15 wherein said topical nasal dosage is in the form of a nose drop.

20. A method for treating sinusitis comprising the steps of:
  obtaining a prepackaged container containing an oral dosage which includes an antibiotic, a topical nasal dosage, and indicia and instructions for the administration of said oral dosage and said topical nasal dosage as an at least ten-day sinusitis treatment regimen; and
  taking said dosage units in accord with said indicia and said instructions.

21. The method of claim 20 wherein said topical nasal dosage includes at least one therapeutic agent selected from the class consisting of saline, hypertonic saline, decongestant, corticosteroid, and antihistamine.

* * * * *